(12) United States Patent
Graff et al.

(10) Patent No.: US 8,756,999 B2
(45) Date of Patent: Jun. 24, 2014

(54) ULTRASONIC PROBE

(75) Inventors: Alfred Graff, Essen (DE); Gert Fischer, Wachtendonk (DE); Karl-Heinz Breckel, Duisburg (DE); Jochen Berkemeier, Hamm (DE)

(73) Assignee: Salzgitter Mannesmann Line Pipe GmbH, Siegen (DE)

( * ) Notice: Subject to any disclaimer, the term of this patent is extended or adjusted under 35 U.S.C. 154(b) by 370 days.

(21) Appl. No.: 13/146,321

(22) PCT Filed: Jan. 14, 2010

(86) PCT No.: PCT/DE2010/000052
§ 371 (c)(1),
(2), (4) Date: Oct. 13, 2011

(87) PCT Pub. No.: WO2010/085936
PCT Pub. Date: Aug. 5, 2010

(65) Prior Publication Data
US 2012/0137779 A1    Jun. 7, 2012

(30) Foreign Application Priority Data
Jan. 27, 2009 (DE) .......................... 10 2009 006 557

(51) Int. Cl.
*G01N 29/28* (2006.01)

(52) U.S. Cl.
USPC .............................................. 73/632; 73/644

(58) Field of Classification Search
USPC ..................... 73/644, 628, 632, 44
See application file for complete search history.

(56) References Cited

U.S. PATENT DOCUMENTS

| | | | |
|---|---|---|---|
| 3,913,386 A | 10/1975 | Saglio | |
| 4,020,679 A | 5/1977 | Barry | |
| 4,058,000 A * | 11/1977 | Ries et al. | 73/644 |
| 4,458,534 A * | 7/1984 | Kising | 73/642 |
| 4,491,137 A * | 1/1985 | Jingu | 600/461 |
| 4,570,487 A * | 2/1986 | Gruber | 73/624 |
| 4,680,967 A * | 7/1987 | Rost | 73/628 |
| 5,351,546 A | 10/1994 | Terhune | |
| 5,804,730 A * | 9/1998 | Pfannenstiel et al. | 73/622 |
| 5,992,235 A * | 11/1999 | Fischer et al. | 73/617 |
| 6,082,198 A * | 7/2000 | Sabourin et al. | 73/633 |
| 6,125,705 A | 10/2000 | Johnson | |
| 6,578,424 B1 * | 6/2003 | Ziola et al. | 73/632 |

FOREIGN PATENT DOCUMENTS

DE    83 12 595 U1    9/1984
DE    198 60 127 C1    10/2000

* cited by examiner

*Primary Examiner* — J M Saint Surin
(74) *Attorney, Agent, or Firm* — Henry M Feiereisen LLC

(57) ABSTRACT

The invention relates to an ultrasonic probe for the non-destructive testing of metal work pieces, particularly pipes, for transverse defects, comprising a row-shaped arrangement of oscillator elements located on a lead wedge for coupling to the work piece. According to the invention, the lead wedge is designed as a wedge-shaped hollow body, which is filled with fluid and the wedge angle of which is a maximum of 24, and which is arranged on the work piece such that the intromission angle into the work piece is a maximum of 70.

11 Claims, 2 Drawing Sheets

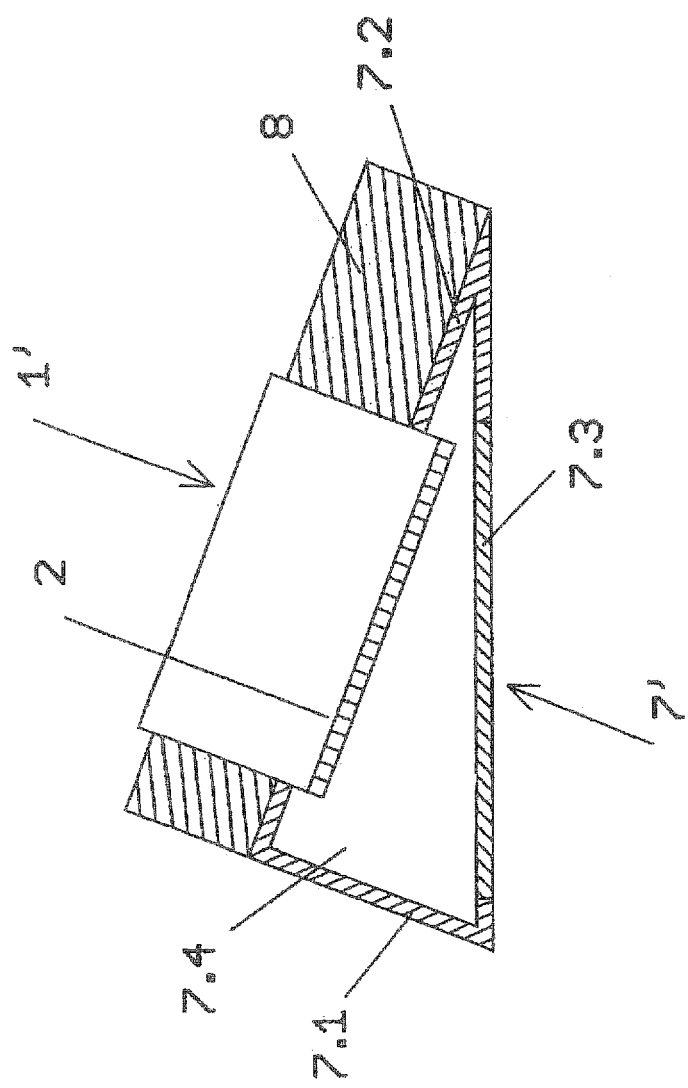

ULTRASONIC PROBE

CROSS-REFERENCES TO RELATED APPLICATIONS

This application is the U.S. National Stage of International Application No. PCT/DE2010/000052, filed Jan. 14, 2010, which designated the United States and has been published as International Publication No. WO 2010/085936 and which claims the priority of German Patent Application, Serial No. 10 2009 006 557.1, filed Jan. 27, 2009, pursuant to 35 U.S.C. 119(a)-(d).

BACKGROUND OF THE INVENTION

The invention relates to an ultrasonic probe for non-destructive testing of metallic workpieces.

A generic ultrasonic probe is known from the utility model G 83 12 595.7. This probe consists of a linear array of oscillator elements which are arranged on a lead wedge made of Plexiglas. The wedge angle of the lead wedge is selected commensurate with the desired propagation direction of the soundwave in the workpiece.

Such probes are used, for example, to test pipes for transverse faults. The transverse fault test of pipes in the 12 o'clock position is a standard technique and is typically implemented by using two opposing probes which emit soundwaves in the direction of the respective other probe.

The probe pair includes either two angled probes or normal probes which couple soundwaves into the pipe at an angle, preferably through water coupling.

The pipe surface can be completely tested by moving the pipe, for example in a helical pattern, under the test unit arranged stationarily in the 12 o'clock position; alternatively, the pipe is rotated and the test unit moves linearly across the pipe surface.

To increase the test capacity of the fault test, e.g., for a rapid 100% test, additional probe pairs must be installed and arranged so as to enable testing of the workpiece surface without any gaps.

Because an arrangement of additional probe pairs in conjunction with a space-saving design frequently increases constructive expenditures, the multi-oscillator rulers (MFS rulers) known from the aforementioned utility model provide an attractive alternative.

MFS rulers are a plurality of ultrasound oscillators which are arranged closely spaced in a housing in form of a linear array, wherein the size of the oscillators depends on the type of the test to be performed.

So-called pulsed oscillators have been developed (DE 19860127 C1) to prevent gaps in the test which inherently unavoidable in this kind of test.

For the transverse fault test, the angle of incidence of the sound waves is maximally 70°, typically only 45°. Because MFS rulers are typically constructed as normal probes, the MFS ruler must be placed for angled incidence at an angle (angle of incidence) relative to the workpiece to be tested. This angle depends on the medium which has a specific sound velocity and can be calculated from the laws of refraction.

For example, the angle of incidence is small for media having low sound velocities, such as water.

Containers filled with water can be used without problem for ultrasound tests with MFS rulers if these containers are attached underneath the pipe (six o'clock test position).

Water containers for coupling are not feasible for a portal solution in a 12 o'clock test position due to the constructive complexity associated with sealing on the tested pipe.

Because the required seal, it is significantly easier to arrange the water containers and the test unit at the six o'clock position; however, the design prevents such an arrangement if the pipe to be tested must be movable on roller tables.

In these applications, the conventional lead wedges entirely made of plastic are typically used. Because of the higher sound velocity of plastic materials compared to water (about 50-100% higher), the wedge angle of the lead wedge is correspondingly greater. In addition to a greater installed height, which may cause constructive problems in some situations, greater wedge angles may also result in significantly longer sound propagation paths, which significantly reduce the echo amplitudes of the sound signal for the known greater damping in plastic compared to water, thus making reliable signal detection significantly more difficult or even impossible.

It is therefore an object of the invention to disclose an ultrasonic probe with a lead wedge and a multi-oscillator ruler for nondestructive testing for transverse faults of metallic workpieces, in particular of pipes, which also allow a simple and reliable ultrasound test on the workpiece in the 12 o'clock position, while simultaneously realizing a small overall height of the probe.

SUMMARY OF THE INVENTION

According to an aspect of the invention, an ultrasonic probe for non-destructive testing of a metallic workpiece, for transverse faults, comprising a wedge having a linear array of oscillator elements for coupling ultrasound emitted by the oscillator elements to the workpiece, wherein the wedge is formed as a wedge-shaped cavity filled with a fluid and having a wedge angle of maximally 24°, which is arranged on the workpiece so that the angle of incidence of the ultrasound soundwaves into the workpiece is maximally 70°.

Advantageously, the employed fluids are media with a smallest possible sound velocity and damping, such as water.

With the proposed solution employing the lead wedge according to the invention, the more advantageous acoustic properties of fluids, mainly sound velocity and damping, can advantageously be used to perform a simple and reliable test for transverse faults.

By using the advantageous properties of, for example, water, a small installation height of the lead wedge can be realized with a rather small wedge angle, while the workpiece can also be tested in the 12 o'clock position without requiring a highly complex seal.

This will become apparent from the following example:
Sound velocity in water at 20° C.: 1483 m/s
Sound velocity in plastic (e.g., Rexolite®): 2311 m/s
Whereas according to the laws of refraction the wedge angle of the lead wedge made of solid plastic is 30.8° for an angle of incidence of the soundwaves of 45°, a wedge angle of only 18.8° is calculated for a water-filled lead wedge, thereby enabling a significantly smaller installation height of the probe. The wedge angles of the lead wedge for other angles of incidence of soundwaves can be computed from Snell's laws of refraction by taking account the sound velocity of the respective medium with which the lead wedge is filled.

Because with water coupling the lead wedge is in direct contact with the surface of the test object, the lead wedge is preferably made of plastic, for example Rexolite®. This has the advantage that the lead wedge can "grind in" on the workpiece surface without damaging the workpiece surface.

According to a preferred embodiment of the invention, the inner surfaces of the side plates and the cover plates of the lead wedge are lined with a sound-absorbing material. This can advantageously prevent interfering ultrasound echoes emanating from the side and cover plates. However, plates made of a suitable solid material can also be used in lieu of the lining.

Additional features, advantages and details of the invention can be inferred from the following description.

BRIEF DESCRIPTION OF THE DRAWING

It is shown in.

DETAILED DESCRIPTION OF PREFERRED EMBODIMENTS

Figure 1:
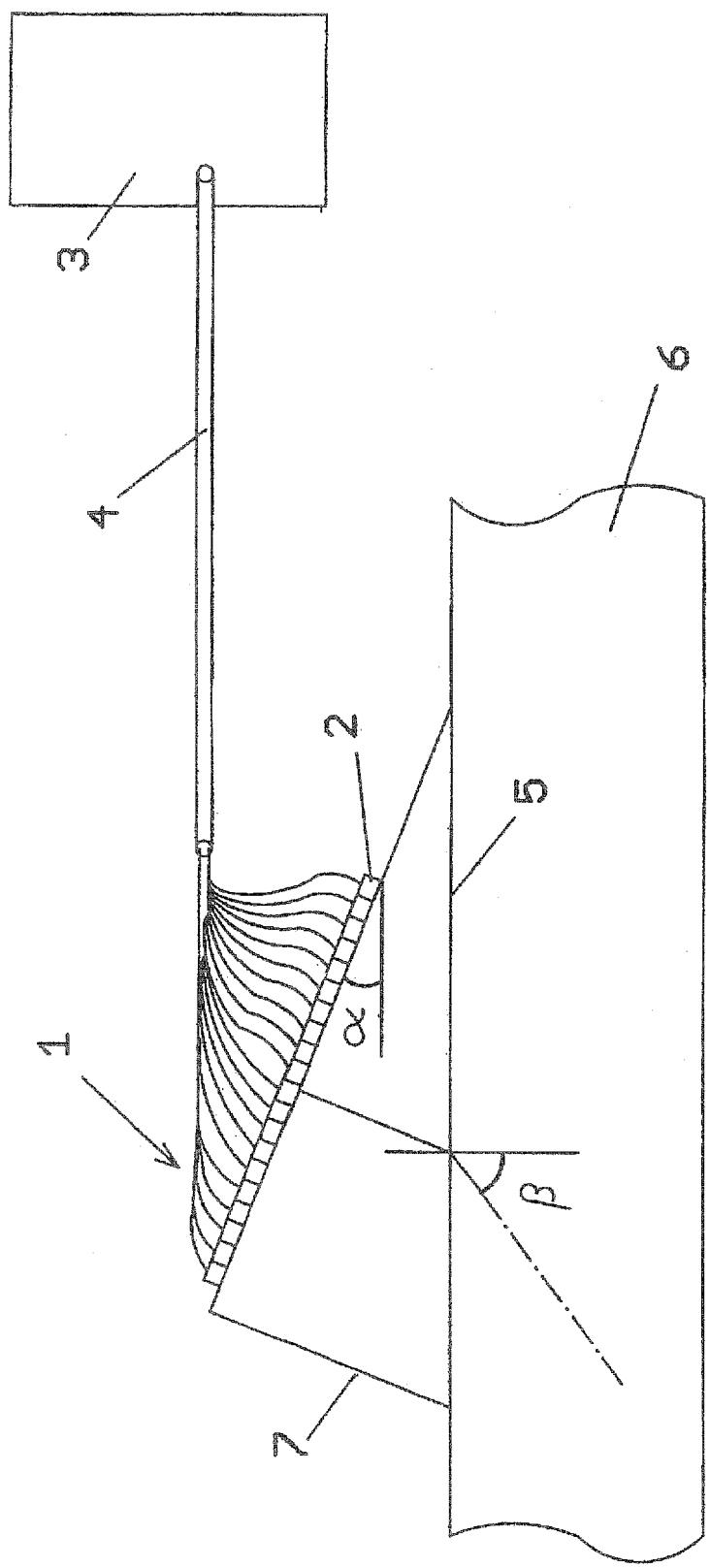
FIG. 1 a schematic view of an ultrasonic probe according to the invention with a fluid-filled cavity as a lead wedge, and FIG. 2 a cross-sectional view of the lead wedge in an alternative embodiment.

FIG. 1 shows a schematic view of an ultrasonic probe according to the invention with a fluid-filled cavity as a lead wedge. The ultrasonic probe 1 includes essentially a multi-oscillator ruler 2 and a wedge-shaped water-filled cavity 7 as a lead wedge. The multi-oscillator ruler 2 and the wedge-shaped cavity 7 are affixed on top of one another by way of an intermediate coupling layer. The individual oscillators of the multi-oscillator ruler 2 are connected via a cable 4 with a probe/evaluation unit 3. The ultrasound is coupled into the workpiece 6 via the coupling surface 5 of the wedge-shaped cavity 7 by way of water wetting.

The illustrated ultrasonic probe 1 is a so-called 45° angle probe, i.e., the angle of incidence β of the soundwaves (angle between the normal on the workpiece surface and the axis of the sound beams) is 45° (FIG. 1).

Because the wedge-shaped cavity 7 is filled with water, the wedge angle α is only 18.8°. The probe 1 can then be built with a very low installation height, thereby significantly simplifying the constructive design for testing in the 12 o'clock position of the pipe, because an otherwise required water container, which is constructively quite complex due to the seal, is no longer required for the test.

FIG. 2 shows in an alternative embodiment a cross-sectional view of the probe 1' according to the invention with a wedge-shaped cavity 7' with a multi-oscillator ruler 2, which is in direct contact with the fluid in the wedge-shaped cavity 7'. The cavity 7' is made of cover plates 7.1 and 7.2, a base plate 7.3 and two side plates 7.4. According to the invention, the individual plates 7.1, 7.2 and 7.4 are made of plastic having sound-absorbing properties for suppressing interfering ultrasound echoes. A suitable material is, for example, Teflon®.

According to the invention, the base plate 7.3 is constructed of a material having good sound-conducting properties and low damping, for example Rexolite®. Alternatively, the plates 7.1, 7.2, 7.4 may also be constructed of Plexiglas provided with suitable sound-absorbing linings.

An (unillustrated) fluidic medium, for example water, is filled in the cavity enclosed by the plates for realizing a water lead path. However, other fluids with a low sound velocity and low damping may also be used.

As an alternative to the arrangement of FIG. 1, an opening may be provided in the cover plate 7.2, in which the ultrasonic probe 1 is inserted with a small play, with the multi-oscillator ruler 2 being in direct contact with the water.

To secure the ultrasonic probe 1' in this position, the probe is provided with a connected frame 8 which has an (unillustrated) seal and rests on the cover plate 7.2, thereby securing the ultrasonic probe 1' and sealing the gap produced by the resulting play against unintentional water leakage.

The water wetting required for high quality coupling of the sound into the workpiece 6 (FIG. 1) can be accomplished, for example, by supplying a steady flow of water to the wedge-shaped cavity 7', which is subsequently fed to the coupling surface 5 by way of an overflow.

The invention claimed is:

1. An ultrasonic probe for non-destructive testing of a metallic workpiece, for transverse faults, comprising a wedge having a linear array of oscillator elements for coupling ultrasound emitted by the oscillator elements to the workpiece,
wherein the wedge is formed as a wedge-shaped cavity filled with a fluid and having a wedge angle of maximally 24°, with the wedge being arranged on the workpiece such that an angle of incidence into the workpiece is at most 70°.

2. The ultrasonic probe of claim 1, wherein the metallic workpiece is a pipe.

3. The ultrasonic probe of claim 1, wherein the angle of incidence of the ultrasound is at most 50°.

4. The ultrasonic probe of claim 1, wherein the angle of incidence of the ultrasound is 45°.

5. The ultrasonic probe of claim 1, wherein the wedge-shaped cavity comprises one or more cover plates, a base plate, and two side plates.

6. The ultrasonic probe of claim 1, wherein the wedge-shaped cavity is made of plastic.

7. The ultrasonic probe of claim 5, wherein interior sides of the one or more cover plates or an interior side of the side plates comprise a sound-absorbing material.

8. The ultrasonic probe of claim 5, wherein the one or more cover plates and the side plates are constructed of a sound-absorbing material and the base plate in contact with the workpiece is constructed of a material having good sound conduction.

9. The ultrasonic probe of claim 5, wherein one of the cover plates has an opening for receiving the ultrasonic probe which is connected with a frame, wherein the frame sealingly rests on the one cover plate and is thereby secured in place.

10. The ultrasonic probe of claim 1, wherein the fluid in the wedge-shaped cavity is selected to have a low sound velocity and a low damping.

11. The ultrasonic probe of claim 1, wherein the fluid inside the wedge-shaped cavity is water.

* * * * *